(12) United States Patent
Ahrens

(10) Patent No.: US 6,322,591 B1
(45) Date of Patent: Nov. 27, 2001

(54) INTRAMEDULLARY OSTEOSYNTHESIS NAIL FOR HEALING FRACTURES OR BONE ELONGATION

(75) Inventor: Uwe Ahrens, Berlin (DE)

(73) Assignee: AAP Implantate AG, Berlin (DE)

( * ) Notice: Subject to any disclaimer, the term of this patent is extended or adjusted under 35 U.S.C. 154(b) by 0 days.

(21) Appl. No.: 09/463,761

(22) PCT Filed: Jul. 30, 1997

(86) PCT No.: PCT/DE97/01672

§ 371 Date: Jan. 31, 2000

§ 102(e) Date: Jan. 31, 2000

(87) PCT Pub. No.: WO99/05981

PCT Pub. Date: Feb. 11, 1999

(51) Int. Cl.[7] .................................................. A61F 2/32
(52) U.S. Cl. .............................. 623/23.27; 606/62; 606/64
(58) Field of Search ..................... 606/62, 63, 64, 606/65, 66, 67, 68, 72; 623/23.15, 23.27, 22.42, 23.43, 22.44, 22.45

(56) References Cited

U.S. PATENT DOCUMENTS

| 5,549,610 | * | 8/1996 | Russell et al. | 606/64 |
| 5,620,445 | * | 4/1997 | Brosnahan et al. | 606/63 |

FOREIGN PATENT DOCUMENTS

| 3308229 | * | 5/1996 | (DE) | 623/23 |
| 4442205 | * | 5/1996 | (DE) | 623/23 |
| 9718776 | * | 5/1997 | (WO) | 623/23 |

* cited by examiner

Primary Examiner—David J. Isabella
(74) Attorney, Agent, or Firm—Cohen, Pontani, Lieberman & Pavane

(57) ABSTRACT

An intramedullary nail system for use in all human and animal bones for healing fractures or lengthening bones, in particular for use in the femoral region, including an intramedullary nail as the base element, which can optionally be connected at its top and/or bottom end to at least one further implant component via connecting members (3, 4, 6, 10).

8 Claims, 1 Drawing Sheet

INTRAMEDULLARY OSTEOSYNTHESIS NAIL FOR HEALING FRACTURES OR BONE ELONGATION

BACKGROUND OF THE INVENTION

1. Field of the Invention

The invention relates to a system, based on an intramedullary nail, for use in all human and animal bones for healing fractures or lengthening bones, in particular for use in the femoral region.

2. Discussion of the Prior Art

Individual solutions are already known for each of the various defects which occur. For example, femoral fractures are cared for using intramedullary nails. Femoral neck nails are used in the event of a femoral neck fracture. These nails are introduced into bores provided in the intramedullary nail and are guided into the femoral neck. The use of special prostheses is known for the knee and hip regions. In the event of a total endoprosthesis change, it is possible to utilize a revision prosthesis.

The abovementioned implants can be used to care for all fractures which occur and to bridge bone removals.

However, the drawback has emerged that a patient with a number of fractures may have to be provided with various types of implants which, however, are incompatible with one another. In the most serious cases, this may lead to a complete change of implant being required in the event of the patients clinical picture changing.

A further drawback which has emerged is that the number of parts which have to be fitted by the operating surgeon is high.

U.S. Pat. No. 5,620,445 discloses an intramedullary nail which, at its distal and proximal ends, can be lengthened by, in each case, one element via threaded or conical connections. One of the extensions has means for attaching instruments for positioning and extracting the intramedullary nail. Both extension elements are provided with bores for guiding through-locking screws.

SUMMARY OF THE INVENTION

The invention is based on the object of providing an implant for providing support during healing of fractures or for bridging bone losses which solves the problems related above.

The basic concept of the invention resides in the fact that a system is provided which works on the basis of an intramedullary nail as the base element, which can be compatibly connected, optionally via connecting means at its top and/or bottom end, to components which can be individually selected by the operating surgeon for the particular clinical picture of the patient and, if appropriate, can be adapted to a changed clinical picture, without a complete change of implant being required in the second case.

Therefore, working on the basis of the intramedullary nail, it is possible, if necessary, to extend the basic implant element into the knee or hip region. It has proven to be of great advantage in this connection that the nail also allows connection to new components which are already implanted, so that it is also possible to extend functions even after the initial operation without having to change the complete implant.

One advantage is that as a type of modular system, the system can at any time when necessary have further components added or even removed. This results for one thing, in reduced operation times and advantages for the patient, since the system can be selected individually according to the patient's clinical picture, even intraoperatively, and can be adapted in the event of the clinical picture changing.

For example, it could be necessary to adapt the implant if, in the event of a tumor being present, parts of the bone have to be removed, but the size of these parts is only determined during the operation. Depending on this result, the operating surgeon can then decide on an individual basis which components are to be attached to the intramedullary nail.

Advantages of the invention also consist in the fact that it is easier and safer to care for fractures by using the inventive system as standard instruments.

The intramedullary nail is preferably a nail with equidistant locking grooves and small target bores over the entire nail length and with two large auxiliary bores at the distal and proximal ends. These auxiliary bores allow the intramedullary nail to be aligned precisely in the beam path of an X-ray appliance and allow the nail to be fixed temporarily, in order for the nail to be fixed definitively in the bone by means of fixing pins which are introduced into the grooves. Alignment solely by means of grooves is only possible with difficulty, since, in contrast to a circular bore, a groove always appears as a groove in the beam path, irrespective of whether or not orthogonality has been established. In this context, the term orthogonality is understood to mean that the bore is aligned at right angles to the beam path and thus appears as a complete circle. The external grooves make the intramedullary nail more flexible and thus allow forces to be introduced more effectively into the bone.

The intramedullary nail, as the base element of the system according to the invention, is matched to the anatomical shape of the bone and may optionally be implanted at the proximal or distal end.

The invention provides for connecting means to be provided at both ends of the intramedullary nail, in order in this way to cover the maximum possible range of indications, i.e. to allow the intramedullary nail base element to be extended both into the knee region and the hip region.

These connecting means are preferably designed as internal or external cones or as screw connections.

However, it is quite possible for the intramedullary nail to be used as a standard locking nail without the connection of other components.

The intramedullary nail can be removed if a rod-like device is screwed or attached to a nail-connecting means, and the nail is then pulled out of the bone after the locking screws have been removed. In doing so, it should be ensured that a retaining element is present when the rod-like removal device is being attached, in order to ensure thereby that there are no torques transmitted into the bone.

A further aspect of the invention provides a support element which can be used in particular as a component for the system according to the invention.

This support element combines a plurality of individual parts which would otherwise be required: it is used to hold and fix, for example, a femoral neck nail, which is then driven through the femoral neck into the femoral head.

The support element has a special implant component for the intramedullary nail of the system as described above as one or more entry holes and in each case a plurality of exit holes which are arranged at a suitable angle, preferably on the opposite side, with respect to each entry hole, so that the nail can be guided through the support element at an angle which can be selected during introduction. At its bottom end, the support element can be connected via a connecting means to the intramedullary nail, preferably via a conical connection.

Preferably, the paths for the femoral neck nail have a profile which is matched to the nail and is advantageously not circular, in order in this way to counteract rotation of the femoral neck nail.

Preferably, in each case three exit holes are provided in the support element. Their center axes may intersect one another at one point. The angle ratio of the entry hole to the exit holes may be set in such a way that the rotational point of the nail which is to be introduced coincides with the entry hole, although it may also lie at other points.

In addition to the support element, various prosthesis elements are provided as further components for the system according to the invention. One example of such elements is the hip-side prosthesis attachment. It is used in combination with the intramedullary nail as, for example, a revision prosthesis.

Similarly, a knee-side prosthesis component may be attached to the bottom end of the nail. This likewise serves, in combination with the intramedullary nail, as, for example, a revision prosthesis. To bridge large defects, it is also possible to use both prosthesis components together.

Finally, an intramedullary nail can also be supplemented, for example in the event of bone loss, by an extension piece of the same type.

BRIEF DESCRIPTION OF THE DRAWINGS

The invention is to be described in more detail below with reference to an example. In the drawing.

DETAILED DESCRIPTION OF THE PREFERRED EMBODIMENTS

Figure 1:
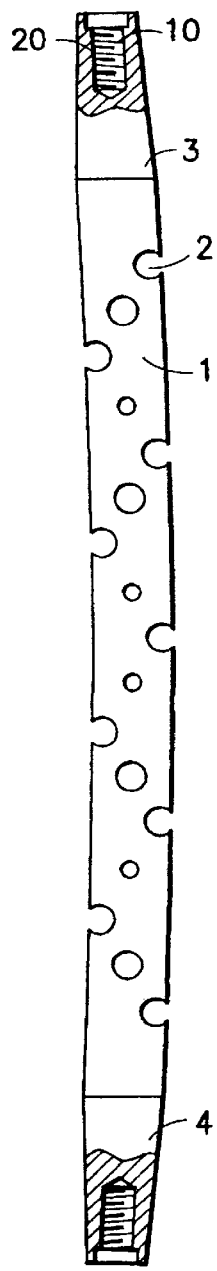
FIG. 1 shows an intramedullary nail as the basic element of the system according to the invention.

FIG. 1 shows a known intramedullary nail 1, as is already used as a tibia nail. It is correspondingly larger when used in the femoral region. The intramedullary nail 1 has external grooves 2 and smaller and larger bores, some of which are used as auxiliary bores making it easier to align the intramedullary nail in the beam path. The intramedullary nail base element has connecting means 3, 4 and 10 at its top and bottom ends. The components can be attached in a form-and/or force-fitting manner via these connecting means. The connecting means shown here are designed as cones or screw threads 20.

Figure 2:
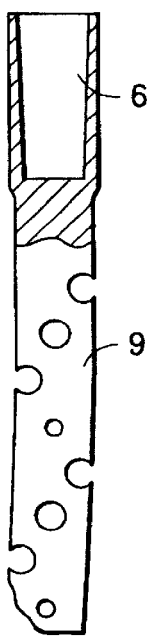
FIG. 2 shows a partial excerpt from FIG. 1, with an internal cone as connecting means, which may be attached to an extension piece.

In FIG. 2, the connecting means shown is an internal cone 6 which, when situated on an extension piece 9, can be attached to the external cone shown in FIG. 1.

Figure 3:
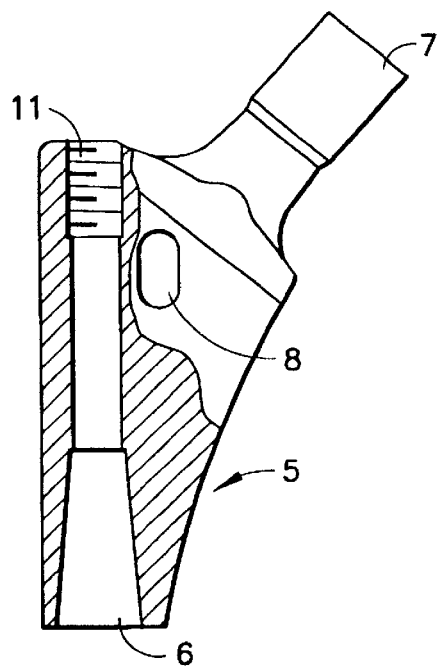
FIG. 3 shows a support element with a hip-side head and femoral neck replacement.

FIG. 3 shows the support element 5 which can be connected to the intramedullary nail 1 by means of the internal cone 6. The support element 5 is provided with a hip-side prosthesis attachment 7. The support element 5 also has further connecting means 11 for connection to further components.

The slot 8 is intended to accommodate a locking screw, so that the moments which are introduced into the component can be transmitted to the bone. This counteracts the possibility of diaphysial dislocation.

Figure 4:
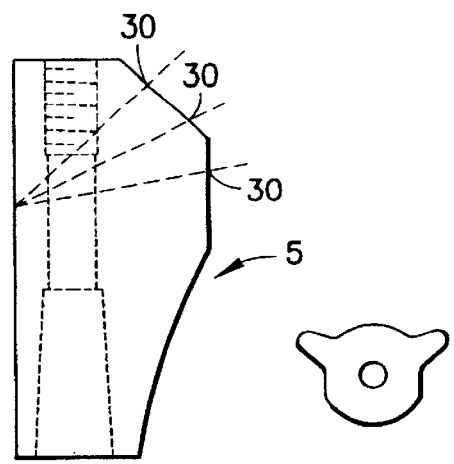
FIG. 4 shows the support element with possible positions of a femoral neck nail which is to be introduced.

FIG. 4 shows the support element 5 and various possibilities for guiding through a femoral neck nail. These nails are used to care for fractures which extend, for example, through the two osseous prominences (pertrochanteric).

The nail which is to be introduced into the support element 5 projects through the femoral neck into the femoral head and thus forms a projecting arm which absorbs flexural and rotational forces in this region. The support element 5 has one entry hole and a plurality of exit holes 30. The femoral neck nail can thus be held in one of the selectable angular positions.

The cutouts in the support element have the same profile as the corresponding nail.

Figure 5:
FIG. 5 shows a cross section through a femoral neck nail.

FIG. 5 shows a modified known profile of a femoral neck nail.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. An intramedullary nail system for healing fractures and lengthening bones, comprising: an intramedullary nail having grooves and bores and a proximal end and a distal end;

a support element connected to at least one of the proximal end and the distal end of the intramedullary nail; and connecting means for connecting the support element to the intramedullary nail, the support element having one of:

at least one entry hole and a plurality of exit holes into which a nail is inserted, the position of the exit holes with respect to the entry hole being such that the nail is insertable at various angles between a longitudinal axis of the nail and the intramedullary nail axis;

a prosthesis attachment; and a nail extension.

2. An intramedullary nail system as defined in claim 1, wherein the connecting means of the intramedullary nail is a conical surface formed on at least one end of the nail.

3. An intramedullary nail system as defined in claim 2, wherein the connecting means is one of an internal conical surface and an external conical surface.

4. An intramedullary nail system as defined in claim 1, wherein the connecting means of the intramedullary nail includes screw threads formed on at least one end of the nail.

5. An intramedullary nail system as defined in claim 1, and further comprising further connecting means at an end of the support element which is remote from the intramedullary nail for connection to further components.

6. An intramedullary nail system as defined in claim 1, wherein the support element has at least three exit holes for the nail.

7. An intramedullary nail system as defined in claim 1, wherein the support element includes a hole for introduction of a locking screw for transmitting moments to the bone.

8. An intramedullary nail system as defined in claim 7, wherein the hole for the locking screw is a slot.

\* \* \* \* \*